United States Patent [19]

Fletcher

[11] Patent Number: 4,525,459

[45] Date of Patent: * Jun. 25, 1985

[54] NEW PURIFIED GLYCOPROTEINS AND USE IN DIAGNOSING INFECTIOUS MONONUCLEOSIS

[75] Inventor: Mary A. Fletcher, Miami, Fla.

[73] Assignee: University of Miami, Coral Gables, Fla.

[*] Notice: The portion of the term of this patent subsequent to Jul. 17, 2001 has been disclaimed.

[21] Appl. No.: 343,235

[22] Filed: Jan. 27, 1982

[51] Int. Cl.³ .................. G01N 33/50; B01J 39/06; B01J 41/06; B01D 9/02

[52] U.S. Cl. .................................. 436/544; 436/545; 436/546; 436/8; 436/87; 436/804; 436/812; 260/112 R; 424/1.1; 424/88

[58] Field of Search ................. 424/1.1; 436/520, 522, 436/8, 501, 503, 504, 63, 87, 804, 812, 815; 260/112 R, 112 B; 435/2

[56] References Cited

U.S. PATENT DOCUMENTS

| | | | |
|---|---|---|---|
| 3,426,123 | 2/1969 | Hoff | 436/521 |
| 3,639,558 | 2/1972 | Csizwas | 436/519 |
| 3,708,572 | 1/1973 | Petoom | 436/521 |
| 3,826,821 | 7/1974 | Zichis | 436/536 |
| 3,840,655 | 10/1974 | Lerner | 436/520 |
| 3,857,931 | 12/1974 | Hager | 436/509 |
| 3,882,224 | 5/1975 | Forgione | 436/511 |
| 3,959,456 | 5/1976 | Zichis | 436/536 |
| 4,046,723 | 9/1977 | Dorman | 524/498 |
| 4,132,769 | 1/1979 | Osther | 436/543 |
| 4,228,148 | 10/1980 | Zichis | 436/536 |
| 4,397,959 | 8/1983 | Hechemy | 436/509 |

OTHER PUBLICATIONS

Paul, J. R., et al., *Am. J. Med. Sci.* 183, 90 (1932), The Presence of Heterophile Antibodies in Infectious Mononucleosis.

Davidsohn, I. et al., *Am. J. Clin. Path.* 5, 455 (1935), The Nature of the Heterophilic Antibodies in Infectious Mononucleosis.

Stuart, C. A., et al., *Proc. Soc. Exp. Biol.* 34, 212 (1936), A Thermostable Antigen in Beef-Cells.

Beer, P., *J. Clin Inrest.* 15, 591 (1936), The Heterophile Antibodies in Infectious Mononucleosis and After the Injection of Serum.

Callahan, H. J., *Int. Archs. Allergy Appl. Immun.* 51, 696 (1976), Preparation of an Infectious Mononucleosis Receptor from Sheep Erythrocyte Stroma.

Gurtler, L. G. et al., *Anim. Blood Grps. Biochem. Genet.* 9, 41 (1978), Presence of Horse Blood Group Antigens in the Major Glycoprotein Fraction of the Erythrocyte Membrane.

Fujita, S. et al., *Biochem. Biophys. Acta.* 406, 206 (1975), Isolation and Partial Characterization of the Major Glycoproteins of Horse and Swine Erythrocyte Membranes.

Grout, D. L. et al., *J. Biol. Chem.* 242(17), 3912 (1967), Isolation and Characterization of M-1 and M-2 Glycoprotein from Bovine, Procine and Avian Plasmas.

Hamazaki, H. et al., *Comp. Biochem. Physiol.* 55B, 37 (1976), Comparative Studies of Human, Equine, Porcine and Bovine Erythrocyte Membrane Sialoglycoproteins.

Evans, A. S. et al., *J. Infect. Dis.* 132, 546 (1975), A Prospective Evaluation of Heterophile and Epstein-Barr Virus-Specific IgM Antibody Tests in Clinical and Subclinical Infectious Mononucleosis: Specificity and Sensitivity of the Tests and Persistence of Antibody.

Fletcher, M. A. et al., *J. Immunol.* 107, 842 (1971), Immunochemical Studies of Infectious Mononucleosis: Isolation and Characterization of Heterophile Antigens from Hemoglobin-Free Stroma.

Levey, B. A. et al., *J. Clin. Microbio,* 11, 256 (1980), Latex Test for Serodiagnosis of Infectious Mononucleosis.

Fletcher, M. A. et al., *J. Immunol.* 117, 722 (1976), Immunochemical Studies of Infectious Mononucleosis: Isolation and Characterization of a Glycoprotein from Goat Erythrocyte Membranes.

Springer, G. F., et al., *Proc. Soc. Exp. Biol.* 96, 103 (1957), Specific Release of Heterogenetic "Mononucleosis Receptor" by Influenza Viruses, Receptor Detroying Enzyme & Plant Proteases.

Singer, et al., *Science* 175, 720 (1972), The Fluid Mosaic Model of the Structure of Cell Membranes.

Gray, W. R. *Methods Enzymol.* 25, 333 (1972), Sequence Analysis with Dansyl Chloride.

Woods, K. R. et al., *Biochem. Biophys. Acta.* 133, 369 (1967), Separation of Dansyl-Amino Acids by Polyamide Layer Chromatography.

Hunter, W. M. et al., *Nature* 194, 495 (1962), Preparation of Iodine-131 Labelled Human Growth Hormone of High Specific Activity.

Fraker, P. J. et al., *Biochem. Briophys. Res. Comm.* 80, 849 (1978), Protein and Cell Membrane Iodinations with a Sparingly Soluble Chloroamide, 1,3,4,6-Tetrachloro-3a,6a-Diphenylglycoluril.

Bolton, A. E. et al., *Bichem J.* 133, 529 (1973), The Labelling of Proteins to High Specific Radioactivities by Conjugation to a $^{125}$I-Containing Acylating Agent.

Kennedy, J. H. et al., *Clinica Chemica Acta* 70, 1 (1976), Protein-Protein Coupling Reactions and the Applications of Protein Conjugates.

Fletcher, M. A. et al., *J. Immunol. Methods* 14, 51 (1977), Immunochemical Studies of Infectious Mononucleosis, VI. A Radioimmunoassay for the Detection of Infectious Mononucleosis Heterophile Antibody and Antigen.

Hamaguchi, H. et al., *Biochem. Biophys. Res. Comm.* 47, 459 (1972), Solubilization and Comparative Analysis of Mammalian Erythrocyte Membrane Glycoproteins.

Fletcher, M. A. et al., *Fed. Proc.* 37, 1438 (1978), Glycoprotein from Sheep Erythrocyte Membrane which Inhibits E Rosette Formation.

Fletcher, M. A. et al., *Immunochemical Studies of Infectious Mononucleosis: VIII. A Glycoprotein from Sheep Erythrocyte with Sialic-Acid-Dependent Receptor Properties, Manuscript Copy, Manuscript Published on or about Feb. 1982 in J. Immunol. 128(2), 976 (1982).
A Lymphocyte Binding Protein, Fourth International Congress of Immunology 7.5.12, 1980.
Grimwood et al, Exper. Parasit., vol. 48, pp. 282–286 (1979).
Fletcher et al., J. Immunol., vol. 107, pp. 842–853 (1971).
Fletcher et al., Biochim. Biophys. Acta., vol. 278, pp. 163–174 (1972a).
Fletcher et al., Fed. Proc., vol. 31 (2), p. 761 Abstract 3080 (1972b).
Caldwell, K. E. et al., Molecular Immunology, vol. 19 (6), pp. 779–791 (6–1982).
Hunter et al., Arch. Biochem Biophys., vol. 163(2), pp. 581–588 (1974).
Dejter-Juszynski et al., Eur. J. Biochem., vol. 83, pp. 363–373 (1978).
T. M. Lo et al., Fed. Proc. 38 (3 Part 1), p. 941, Abstract 3761 (1979).
Levey et al., J. Clin. Micro, vol. 11, pp. 256–262 (1980).
Latif et al., Fed. Proc., vol. 40 (3 Part 1), p. 355, Abstract 699 (1981).
Fletcher et al., J. Immunology, vol. 128 (2), pp. 976–982 (2–1982a).
Fletcher et al., Clin. Exp. Imm., vol. 14, pp. 607–614 (1974a).
Fletcher et al., Proc. Soc. Exp. Biol. Med., vol. 145, pp. 1100–1105 (1974b).
Fujita et al., Biochim. Biophys. Acta., vol. 406, pp. 206–213 (1975).
Fletcher et al., J. Immunology, vol. 117 (3), pp. 722–729 (1976).
Fletcher et al., Fed. Proc., vol. 33 (3 Part 1), p. 777, Abstract 3214 (1974c).
Fletcher et al., J. Immun. Meth., vol. 14, pp. 51–58 (1977b).
Merrick et al., Fed. Proc., vol. 36 (3), p. 702, Abstract 2269 (1977).
Fletcher et al., Fed. Proc., vol. 37, p. 1438, Abstract 930 (1978).

*Primary Examiner*—Ben R. Padgett
*Assistant Examiner*—M. Moskowitz
*Attorney, Agent, or Firm*—Memel, Jacobs, Pierno, Gersh & Ellsworth

[57] ABSTRACT

Preparations useful in the diagnosis of infectious mononucleosis are disclosed. Horse and sheep erythrocytes are purified and essentially homogenous glycoproteins are extracted. The purified glycoproteins are useful as antigens in testing for the presence of the heterophile antibodies of infectious mononucleosis and in the preparation of reagents for the enumeration of rosetting lymphocytes without having to have available fresh sheep blood.

20 Claims, No Drawings

NEW PURIFIED GLYCOPROTEINS AND USE IN DIAGNOSING INFECTIOUS MONONUCLEOSIS

FIELD OF THE INVENTION

This invention relates to purified erythrocyte membrane glycoproteins from mammals such as horse and sheep, a method of using these preparations in immunoassays for the detection of infectious mononucleosis heterophile antibody and the usefulness of these glycoproteins in the preparation of a stable, standardizable reagent for the enumeration of rosetting lymphocytes.

The U.S. government has a paid-up license in this invention and the right in limited circumstances to require the patent owner to license others on reasonable terms as provided for by the terms of Grant No. AM 16763 awarded by the National Institutes of Health.

BACKGROUND OF THE INVENTION

Glycoproteins are multipurpose glycoconjugates present in all forms of life. The ramifications of their prevalence in biological studies involving cell surface membranes are under active investigation. Glycoproteins are currently believed to be key factors in cellular function and communication. In the present invention, certain highly purified erythrocyte glycoproteins have been identified as the antigenic substances responsible for the hemolysis and hemagglutination of appropriate erythrocytes by suitably adsorbed serum in methods for the detection of infectious mononucleosis (IM) antibody.

Paul and Bunnell reported in their now historic piece of investigative research that non-specific antibodies in the form of hemolysins and agglutinins from sheep cells were present in abnormally high concentrations in the serum of patients during the acute stages of infectious mononucleosis. *Am. J. Med. Sci.* 183, 90–104 (1932). These sheep cell agglutinating antibodies were heterophilic in nature but were not of the "Forssman-type". Heterophilic antibodies were defined as those having the ability to react with a number of antigens that were apparently unrelated to those that stimulated their production. The "Forssman-type" antibodies were defined as those that were reactive with the erythrocytes of sheep and the heterophilic antigens produced by guinea pig kidney [Davidsohn, I. and Walker, P. H., *Am. J. Clin. Path.* 5:445–465 (1935)]. Many assays that detect heterophile antibodies have been developed. See, e.g., U.S. Pat. Nos. 3,426,123 and 3,708,572.

Stuart et al and Beer reported that horse erythrocytes also reacted with the heterophile antibodies found in sera of patients with infectious mononucleosis. See *Proc. Soc. Exp. Biol.* 34: 212, 215 (1936) and *J. Clin. Invest.* 15:591–599 (1936).

These observations have provided the basis for the immunochemical diagnosis of infectious mononucleosis through the isolation and purification of glycoprotein from mammalian erythrocytes.

Workers have reported an infectious mononucleosis receptor isolated from sheep erythrocyte stroma. The receptor is a glycoprotein whose antigenic determinant is closely related to the presence of sialic acid. [Callahan, H. J., *Int. Archs. Allergy Appl Immun.* 51:696–708 (1976)]. This investigator used a hemoglobin containing stroma which was denatured in the reaction mixture such that hemoglobin contamination could never be completely removed from the glycoprotein product. The initial sheep erythrocyte preparation was prepared by a hot phenol extraction method. In the present invention the applicant extracted the glycoprotein from sheep and horse erythrocytes with hot ethanol. The resulting glycoprotein product is pure and has a high reactivity with the IM heterophile antibody.

Glycoprotein fractions have been isolated from horse by chloroform methanol extraction. These fractions were closely associated with certain blood group antigens. [Guertler, K. G., Schmid, D. O., Yebou, D. A. and Cleve, H., *Blood Grps. Biochem. Genets.* 9:41–45 (1978)]. However, the product obtained was not tested for reactivity with IM or other P-B positive antibodies. A close examination of the reported data revealed that the isolated glycoprotein was probably impure and was hence unsuitable for use in assays as sensitive as radioimmunoassays. Other investigators have reported glycoproteins isolated from various mammalian species and have obtained "purified" glycoprotein. For example, Hamaguchi and Cleve reported a method of isolating glycoprotein from human, ox, swine, horse and sheep erythrocytes by chloroform-methanol extraction. However, the isolated extract was crude by comparison to the purified glycoprotein of this invention The serological activity of the Hamaguchi preparation were about 1000-fold less than that of this invention. [See also Fujita, S., Cleve, H., *Biochim. Biophys. Acta* 406:206–213 (1975); Grant, D. C. Martin, W. G. and Anastassiadis, P. A., *J. Biol. Chem.* 242(17):3912–3918 (1967); Hamazaki, H., Hotta, K, Konishi, J., *Comp. Biochem. Physiol.* 55 B:37–44 (1976)].

An important criterion for the diagnosis of infectious mononucleosis has been based on erythrocyte agglutination or complement mediated hemolysis of blood cells from several species such as goat, horse, bovine and ox.

Bovine erythrocytes were found to have a high specificity for the IM heterophile antibody. Investigators believed that bovine erythrocytes contained immunological determinant(s) which bound more specifically to heterophile antibodies than the immuno-determinants present in erythrocytes from other species [Evans, A. S., et al *J. Infect. Dis.* 132:546–554 (1975)].

As early as 1971, the present inventor and coworkers [Fletcher, M. A., and Woolfolk, B. J., *J. Immunol.* 107:842–853 (1971)] found that the partial purification of bovine erythrocytes with 75% ethanol yielded a crude glycoprotein extract which showed high reactivity with heterophile antibodies. The reactivity was based on the result of each of three test methods which measured hemagglutination inhibition, quantitative precipitation and agar gel diffusion.

Several diagnostic tests for IM have been reported that are based on bovine erythrocyte antigens and which employ crude extracts as the purest form of the reactive principle in bovine erythrocytes. For example, see U.S. Pat. Nos. 3,826,821; 3,840,655; 3,959,456 and 4,228,148.

The applicant has purified the bovine erythrocyte membrane glycoprotein to an essentially homogeneous form. The homogeneity of this bovine glycoprotein was shown in several ways, including polyacrylamide gel electrophoresis in the presence of sodium dodecyl sulfate. The purified form of this bovine glycoprotein for IM detection resulted in at least a ten-fold increase in sensitivity in hemagglutination inhibition tests relative to the results obtained with the crude extract of bovine erythrocytes described by Fletcher et al in the year 1971. The results obtained with this glycoprotein in partially purified form were reported on Mar. 27, 1980 by the present inventor and co-workers in Levey B. A. et al, *J Clin. Microbio.* 11, 256–262 (1980).

The partially purified and homogeneous bovine glycoprotein products have also been described in a pending application: U.S. Ser. No. 247,934, filed Mar. 26, 1981.

The present invention involves the isolation of antigens from horse and sheep erythrocyte glycoprotein which react with IM but not with Forssman antibodies. The IM activity is associated with certain sialoglycoproteins and is completely abolished by neuraminidase treatment. The glycoproteins carry the antigenic determinant responsible for the reaction with the Paul-Bunnell antibody. This characteristic has made possible the development of certain serological diagnostic tests for IM which have heretofore required intact erythrocytes and complicated, time consuming adsorption procedures. See, for example, Levey et al., supra.

An additional receptor property of the glycoproteins isolated here is their ability to interact with peripheral blood lymphocytes forming "E rosettes" in vitro. An "E rosette" is a peripheral blood lymphocyte to which three or more sheep red blood cells have become attached. Rosetting is an accepted marker for human T lymphocytes and thymocytes. In this invention the receptor which is responsible for rosetting has been isolated from sheep and horse erythrocyte glycoprotein. Thus, the purified reagent may be useful in the preparation of a standardizable reagent for the enumeration of rosetting lymphocytes.

SUMMARY OF THE INVENTION

The products of this invention provide highly purified erythrocyte glycoprotein from sheep and horse erythrocyte membranes. The glycoproteins carry the antigenic determinant for the Paul-Bunnell heterophile antibody of infectious mononucleosis and they do not possess cross reactivity for other human antibodies. This particular characteristic of the glycoproteins make them useful in the development of serologic diagnostic tests for infectious mononucleosis because this methodology eliminates the step of absorbing the sera on guinea pig kidney prior to proceeding with diagnostic testing for IM.

The homogeneous, highly purified erythrocyte glycoproteins of this invention provide stable, standardizable reagents which will keep indefinitely at room temperature without loss of biological activity. These glycoproteins may be attached to inert supports and may also be labeled with tags such as radioactive tags, and used in immunoassays such as radioimmunoassays, for the detection of the Paul-Bunnell antibody and for the detection of certain subpopulations of lymphocytes.

A special embodiment of this invention involves a receptor property of the isolated glycoprotein of sheep and horse erythrocytes which is the ability of this receptor to interact with human T lymphocytes, and thus to inhibit the formation of rosettes. The formation and the enumeration of rosetting lymphocytes required the availability of fresh sheep blood which requires special handling for shipping and storage. In addition, fresh sheep blood has limited shelf life even when stored at 4° C.

The amino acid composition of the purified horse erythrocyte glycoprotein in moles per 100 moles is as follows: Aspartic acid about 8.1, Threonine about 10.6, Serine about 10.8, Glutamic acid about 9.4, Proline about 12.3, Glycine about 9.2, Alanine about 11.3, Valine about 4.4, Methionine about 0.8, Isoleucine about 3.5, Leucine about 8.2, Tyrosine about 1.1, Phenylalanine about 2.9, Histidine about 1.2, Lysine about 1.3, and Arginine about 4.8. The composition of threonine has been corrected for about a five percent loss on hydrolysis and that of serine has been corrected for about a ten percent loss on hydrolysis.

The amino acid composition of the purified sheep erythrocyte glycoprotein in moles per 100 moles is as follows: Aspartic acid about 5.6, Threonine about 8.1, Serine about 12.9, Glutamic acid about 13.0, Proline about 11.6, Glycine about 7.7, Alanine about 9.6, Valine about 6.2, Methionine about 0.5, Isoleucine about 4.6, Leucine about 8.3, Tyrosine about 4.6, Phenylalanine about 1.2, Histidine about 1.6, Lysine about 3.2, Arginine about 4.0, and Tryptophan about 0.3. Carbohydrates account for fifty-five percent of the purified horse erythrocyte glycoprotein and for approximately fifty-seven percent of the purified sheep erythrocyte glycoprotein.

DETAILED DESCRIPTION OF THE INVENTION

The product described here is a purified glycoprotein useful as a diagnostic reagent in the detection of infectious mononucleosis. The product purity achieved by this invention provides a level of antigenic sensitivity and specificity which has not heretofore been possible with other IM diagnostic preparations. The antigens described here were isolated and purified from sheep and horse erythrocyte membrane glycoprotein in a series of steps which involved phosphocellulose chromatography, ethanol precipitation, lipid solvent extraction and diethyl amino ethyl (DEAE) chromatography.

The sheep and horse glycoproteins bear an immunodeterminant which is responsible for the reaction of the sheep erythrocyte with the Paul-Bunnell antibody of IM. Specificity of the isolated antigens seems to be directly related to the presence of terminal sialic acid residues. Sialic acids are also responsible for the reactivity of the glycoconjugates with peripheral blood lymphocytes.

The structures of these erythrocyte glycoproteins have been studied extensively by the applicant. Electron microscopic studies of the glycoprotein preparations have revealed that the sheep glycoprotein has an asymetrical structure comprised of aggregates with an average diameter of 7.1±2.2 nanometers. The horse glycoprotein appeared as uniform globular aggregates with an average diameter of 9.3±16 nanometers. The apparent aggregate molecular weights as calculated by the applicant are 167,000 daltons for the sheep glycoproteins and 383,000 daltons for the horse glycoprotein.

The applicant determined the apparent subunit molecular weight of the glycoconjugates by measuring the mobility of the glycoprotein by sodium dodecyl sulfate polyacrylamide gel electrophoresis (SDS-PAGE) at graduated gel concentrations. The horse glycoprotein gave a single major band staining with periodic acid Schiff reagent (PAS) and with coomassie blue (CB). The apparent molecular weight calculated from the retardation coefficient was 30,000 daltons. The sheep glycoprotein gave a major band and a small amount of a much faster moving component with the CB stain. However, with PAS stain two minor components could be observed. The apparent molecular weights of the glycoprotein subunits were calculated from the retardation coefficient. Eighty percent had an apparent molecular weight of about 26,500 daltons, about 10% had an apparent molecular weight of about 9,000 daltons and about an additional 10% had an apparent molecular weight of about 35,000 daltons. The applicant found that the minor glycoproteins which had apparent molecular weights of about 9,000 and of about 35,000 daltons contained sialic acid and had IM activity equivalent to that of the major glycoprotein.

Data collected by the applicant revealed that the products of this invention were sialoglycoproteins. The study on the nature of the Paul-Bunnell heterophile antigenic determinant by the applicant and other investigators has confirmed that sialic acid is required for glycoprotein specificity (See, e.g., Fletcher and Woolfolk (1971) *J. Immunol.* 107:842–853; Fletcher et al (1976) *J. Immunol.* 117:722–729, and Springer and Rappaport (1957) *Proc. Soc. Exp. Biol.* 96:103–107). Neuraminidase, an enzyme that cleaves sialic acids, had a marked effect on the reactivity of these antigens with the IM heterophile antibody. Neuraminidase treatment resulted in a substantial loss of activity with the Paul-Bunnell antibody.

The following tables partially characterize the composition of the sugars present in the purified product.

TABLE I

Carbohydrate Composition of Horse Erythrocyte Glycoprotein

| Sugar Residue | μmoles/mg glycoprotein (molar ratio) | g/100 g glycoprotein |
|---|---|---|
| N—glycolylneuraminic acid | 0.855 (1.3) | 28.0 |
| Galactose | 0.635 (1) | 11.4 |
| N—acetylgalactosamine | 0.637 (1) | 14.1 |
| N—acetylglucosamine | 0.040 (0.1) | 0.9 |
| Mannose | 0.040 (0.1) | 0.7 |

TABLE II

Carbohydrate Composition of Sheep Erythrocyte Glycoprotein

| Sugar Residue | μmoles/mg glycoprotein | g/100 g glycoprotein |
|---|---|---|
| Sialic Acids | 0.541 | 16.7 |
| Galactose | 0.558 | 9.0 |
| N—acetylgalactosamine | 0.676 | 13.7 |
| N—acetylglucosamine | 0.709 | 14.4 |
| Mannose | 0.104 | 1.7 |

The glycoproteins of this invention are extracted from erythrocyte membrane, the cellular membrane of the red blood cell. Cellular membrane is essentially comprised of lipids. Singer and Nicholson proposed the currently popular mosaic model of the cell membrane. Science (1972) 175:720. In this model, a mosaic of globular proteins is interspersed in a phospholipid bilayer. Thus, there is usually some lipid contamination in purified membrane protein preparations. However, in this invention the complex glycolipid is substantially entirely removed by binding the product on an anion exchange column and eluting with a high salt buffer.

It has been found that the glycolipid removed by this series of steps is essentially nonreactive to antibodies which characterize human infectious mononucleosis. Its removal is of special importance to the achievement of a practical immunoassay method, however, because in these methods, one must be able to assume that the label (whether a radioactive isotope, a fluorogen, a chromogen, a luminescent material or another known type of label) is substantially entirely bound to a specific immunochemical reactant. Inadvertent labelling, even of a material inert to all other substances present, renders this assumption invalid and leads to results that are invalid or unable to be reliably interpreted. Moreover, a labelled contaminant, even if nonreactive with the immunochemical entity being assayed for, may well be reactive with another component in a test sample and hence may contribute to the magnitude of readings obtained, thereby disrupting the assay and causing it to give false information. It is therefore essential to the development of successful immunoassays for diagnosis and monitoring of human IM that the complex glycolipid be essentially completely removed from purified glycoprotein to be used in such immunoassays.

Table III gives the amino acid compositions of the purified horse glycoprotein and the purified sheep glycoprotein in terms of moles per 100 moles of total protein present. Individual amino acids were determined after hydrolysis in 6NHCl at 110° C. in sealed, evacuated tables for 24 hours with a JEOL 5AH amino acid analyzer. N-terminal amino acid analysis was performed by the dansyl method [Gray, W. R. *Methods Enzymol.* 25, 333 (1972)]. DNS-amino acids were identified by TLC as described by Woods, K. R. et al *Biochem. Biophys. Acta.* 133, 369 (1967). For amino acid analysis of the sheep glycoprotein, tryptophan was determined after hydrolysis for 20 hours at 100° C. in 4N methanesulfonic acid.

TABLE III

Amino Acid Composition of Horse Erythrocyte Glycoprotein and of Sheep Erythrocyte Glycoprotein

| Amino Acid | horse, moles/100 moles | sheep, moles/100 moles |
|---|---|---|
| Aspartic Acid | 8.1 | 5.6 |
| Threonine[a] | 10.6 | 8.1 |
| Serine[b] | 10.8 | 12.9 |
| Glutamic Acid | 9.4 | 13.0 |
| Proline | 12.3 | 11.6 |
| Glycine | 9.2 | 7.7 |
| Alanine | 11.3 | 9.6 |
| Valine | 4.4 | 6.2 |
| Methionine | 0.8 | 0.5 |
| Isoleucine | 3.5 | 4.6 |
| Leucine | 8.2 | 8.3 |
| Tyrosine | 1.1 | 4.6 |
| Phenylalanine | 2.9 | 1.2 |
| Histidine | 1.2 | 1.6 |
| Lysine | 1.3 | 3.2 |
| Arginine | 4.8 | 4.0 |
| Tryptophan | — | 0.3 |

[a]corrected for 5% loss on hydrolysis.
[b]corrected for 10% loss on hydrolysis.
Tryptophan was not determined in the horse glycoprotein.

A special embodiment of the present invention requires that a tag be attached either to the antigen to be determined or its binding partner. A radioactive tag is preferred, for example $^{125}I$, $^{131}I$, $^{3}H$ or $^{14}C$, or any other radioisotope easily and conveniently measured. Tritium labeling of proteins, for example, can be carried out with [$^{3}H$]-acetic anhydride, a well known reagent frequently used for this purpose. The isotope $^{125}I$ is the most preferred because of its high specific activity and because of its relatively long half life.

An antibody or proteinaceous antigen can be labeled with $^{125}I$ to a specific activity of about 50 micro Ci/microgram of protein by one of a variety of methods known in the art such as e.g., lactoperoxidase, chloramine-T [Hunter, W. M. et al Nature 194, 405 (1962)], Iodogen [Fraker, P. J. et al *Biochem. Biophys. Res. Comm.* 80, 849 (1978)], or Bolton-Hunter reagent [Bolton, A. E. at al *Biochem. J.* 133, 529 (1973)]. The labelled protein is separated from unreacted free $^{125}$I by gel filtration.

The preferred method of radioactively labelling proteins containing tyrosine is chloramine-T. It is the most frequently used method of labelling proteins with a radioactive tag. Alternatively, one can label tyrosine residues with tritium by the two-step process of first reacting protein with NaI, then catalytically dehydrogenating with tritium gas. The free amino group of the side chains of lysine or of arginine can be labelled with $^3$H-acetic anhydride or with Bolton-Hunter reagent.

A large variety of other tags can be employed instead of radioactive ones. Other methods of tagging include attachment of a fluorogen, chromophore, enzyme or luminescent tag. For example, horse radish peroxidase or beta-galactosidase may be coupled to a proteinaceous antigen by many of the methods discussed in Kennedy, J. H. et al, *Clinica Chimica Acta* 70, 1 (1976). Fluorescein isothiocyanate is a well known fluorogenic group that can be attached to proteins [Ackroyd, J. F. ed., *Immunological Methods*, Blackwells Oxford (1964) pp. 155–174].

A. Preparation of a Crude Antigen from Horse or Sheep Red Blood Cells.

Hemoglobin-free stroma is isolated by extraction of stroma, i.e., membranes, as generally described in Fletcher et al, *J. Imm.* 107, 842 (1971). More particularly, to fresh blood collected by venipuncture from horse or from freshly slaughtered sheep, an anticoagulant is added to prevent clotting. Almost any conventional anticoagulant may be used, except that heparin and ethylenediamine tetraacetic acid must be avoided. Preferred anticoagulants include acidified citrate-dextrose, oxalate and Alsievers. The blood may be stored at normal refrigeration temperatures for up to about 24 hours. It is then thoroughly washed with any of the common isotonic buffers at a pH that preserves the integrity of the cell membrane, i.e., in the order of about 5.0 to about 9.0, preferably about 6.0 to about 8.0, such as phosphate-buffered saline of pH about 7.4, or tris-buffered saline of pH about 7.4. If the blood samples are allowed to stand for a period appreciably longer than about 24 hours prior to washing, the samples may become contaminated with bacteria or with lysosomal enzymes from white blood cells. For each washing step, the cells are suspended in buffer and then centrifuged. After centrifugation, the supernatant and buffy coat are removed by aspiration. These washing-centrifugation-aspiration steps are continued until the buffy coat is substantially completely removed and the supernatant is essentially clear and free from color. It is important to remove substantially all of the buffy coat because it is a source of hydrolytic enzymes. Approximately one quarter of the total volume of erythrocytes is typically lost during the washing steps.

Washed and packed erythrocytes are then lysed in hypotonic buffer of alkaline pH, i.e., above about 8.0. The lysing buffer must be alkaline to prevent denaturation of hemoglobin and unwanted binding of denatured hemoglobin to membranes. Cell stroma or membranes are packed together by centrifugation at about 13,000 xg for 1 hour at a temperature in the order of about 4° to about 15° C. The supernatant is aspirated and discarded, whereupon the loosely packed membrane layer is decanted from the red pellet. This procedure of alkaline washing, followed by cold centrifugation and separation steps, is repeated until the decanted membrane layer is creamy white, i.e., without visible hemoglobin contamination. The purified stroma must then be dried, e.g., by freeze-drying, to carry out the next steps. An alternative method to centrifugation is filtration on Pellicon (Trademark of Millipore), as described by Rosenberry, T. L. et al *J. Biochem. Biophys. Meth.* 4, 39 (1981) for the preparation of membranes from human erythrocytes.

Thereafter, an even suspension in acetone of freeze-dried, hemoglobin-free stroma from horse or sheep erythrocytes is prepared by grinding in a mortar and pestle about 1 gram of stroma with preferably about 200 ml acetone. The acetone must be anhydrous, and taken from a freshly opened bottle. The volume of acetone per gram of stroma may vary from as low as about 100 ml up to a volume substantially greater than 200 ml. The suspension is refluxed, normally for about 3 hours, but the time may vary from about 1 to about 6 hours. The residue is collected by filtering of the acetone while the suspension is still warm; otherwise there is some unwanted precipitation of acetone-soluble neutral lipids on the filter. The residue is thoroughly washed with acetone, preferably warm acetone, and air dried.

The same refluxing procedure is repeated on the acetone extracted residue, this time substituting anhydrous, 100% ethanol for the acetone. Extraction with 100% ethanol removes some but not all of the glycolipids. The ethanol extract is discarded, and the residue is dried. The acetone and ethanol extract residue is refluxed again, preferably with about 75% aqueous ethanol but a solution of between about 50% and about 80% aqueous ethanol may be used. The supernatant is removed by filtration and set aside. The residue is then washed with an equal volume of the aqueous ethanol. The washed residue is discarded. The extract and all the washings are combined, concentrated, dialyzed to remove salt and freeze-dried in a conventional manner. Alternatively, the aqueous ethanol extract and its washings may be combined, concentrated, dialyzed against water and stored under normal refrigeration temperatures.

B. Isolation and Purification of the Horse or Sheep Erythrocyte Glycoprotein

The lyophilized aqueous ethanol extract from Step A is redissolved in water and precipitated with about 90% aqueous ethanol. Incubation on ice for at least two hours and addition of a salt, e.g., 3 or 4 crystals of sodium acetate or other common salt, can help to initiate precipitation. Typically, a massive, white precipitate appears. This precipitate is centrifuged and the supernatant is removed and discarded. The precipitate is then dialyzed against a conventional buffer of low ionic strength and low pH in preparation for passage through a cationic exchange column.

Chromatography on a cationic exchange resin is best performed at a pH of from about 4 to about 6, e.g. above the isoelectric focusing point of the glycoprotein reactive with heterophile antibodies. Resins appropriate for this step include phosphocellulose, carboxymethyl cellulose, or any of the weakly acidic acrylic resins commonly employed for purification of proteins. After the resin is preequilibrated with the low ionic strength and low pH buffer, the dialyzed protein sample is passed through the column. Neutral and basic contaminants are bound by the column and discarded. Those fractions which contain sialic acid and do not bind the column are collected. They can be dialyzed against water and freeze-dried or lyophilized if desired.

The collected fractions, preferably but not necessarily in lyophilized form are treated next. If lyophilized or otherwise dried, the fractions are first dissolved in water, about 5 volumes of diethyl ether: ethanol (in a volume to volume ratio ranging from about 4:1 to about 1:1) are next added and the mixture is centrifuged and permitted to settle. Two phases appear, one aqueous and one comprising diethyl ether. The aqueous layer is removed and freeze-dried to remove residual ether and water.

Another extraction with a different lipid solvent from diethyl ether is then performed, in accordance with conventional techniques of chemistry. In this procedure, the lyophilized extract from the first extraction step is dissolved in water and reextracted in about 9 volumes of chloroform/methanol in the ratio of about 2:1, volume by volume. The mixture is again centrifuged and permitted to separate into an aqueous phase and an organic phase. The separated aqueous phase is removed and lyophilized.

In order to remove contaminants still remaining principally comprising complex glycolipids, the lyophilized glycoprotein is dissolved in a low ionic strength buffer containing about 1% neutral detergent, such as Emulphogen or Triton-X-100. This detergent aids in dissolving the complex glycolipid. The solution is loaded onto an anion exchange column, preequilibrated with low ionic strength buffer. A variety of suitable anion exchange resins are commercially available, including DE-52 cellulose, DEAE BIO-GEL A and Cellex D. The column is washed with the low ionic strength aqueous buffer until the optical density of the fractions eluted has returned to the level of a blank solution consisting of the buffer alone, normally less than 0.1 units at 280 nanometers. The column is then eluted with aqueous buffer containing high salt concentration, i.e. in the order of more than 0.3 molar concentration of a common salt such as NaCl, Na acetate, KCl, and the like. High concentrations of salt compete with the electrostatic interactions between the glycoprotein and the cationic resin, so as to pool a single peak of material. The material is dialyzed against $H_2O$, freeze-dried and held for use.

C. Use of the Purified Glycoproteins of the Present Invention

In experiments conducted by the applicant, the glycoprotein products of this invention were strong inhibitors of the agglutination of sheep erythrocytes by sera from patients with infectious mononucleosis. The receptor properties were abolished by prior treatment of the glycoproteins with neuraminidase. (Table III and Table IV). Also, there was no detectable activity with Forssman agglutinin.

TABLE III

Hemagglutination Inhibitory Activity of Purified Sheep Glycoprotein

| Hemagglutinins | μg/ml completely inhibiting hemagglutinating doses | |
|---|---|---|
| | Glycoprotein | Glycoprotein Neuraminidase treated |
| IM serum[a] | 2 | >5000 |
| Forssman anti- | >5000 | >5000 |

TABLE III-continued

Hemagglutination Inhibitory Activity of Purified Sheep Glycoprotein

| Hemagglutinins | μg/ml completely inhibiting hemagglutinating doses | |
|---|---|---|
| | Glycoprotein | Glycoprotein Neuraminidase treated |
| serum[b] | | |

[a]tested with sheep erythrocytes
[b]tested with papain-treated sheep erythrocytes

TABLE IV

Agglutination Inhibition Studies of Horse Erythrocyte Glycoprotein

| Test System | μg/ml inhibiting four agglutinating doses of IM Serum | |
|---|---|---|
| | Glycoprotein | Glycoprotein Neuraminidase treated |
| Inhibition of agglutination of sheep erythrocytes by IM serum | 0.2 | >5000 |
| Inhibition of agglutination of horse glycoprotein latex reagent by IM serum | 6.3 | Not tested |

Either of the products of this invention is useable in the latex bead test for diagnosing and/or monitoring human infectious mononucleosis.

1. Latex Bead Test

Chemical coupling of either the purified horse glycoprotein or sheep glycoprotein of this invention to a carrier particle can be accomplished in a variety of ways. Particles composed of a synthetic polymer such as polystyrene, poly (methyl methacrylate) or any synthetic latex are preferred over microbial cells due to their enhanced stability during long term storage. In general, the beads or particles should have free functional groups such as one or more of the primary amino, sulfhydryl, carboxyl or hydroxyl groups. Various methods of coupling proteins to carrier particles composed of a synthetic polymer are discussed in the literature, including *inter alia* in U.S. Pat. Nos. 4,046,723; 3,882,224; 3,857,931; 3,639,558. In the preferred method of coupling latex beads to a glycoprotein of this invention, the purified glycoprotein is added to a suspension of about 0.25% (in water) of carboxyl-modified, uniform latex particles. The mixture is stirred for at least about 30 minutes. The pH is maintained between about 4 and about 6. Then a substituted carbodiimide such as, e.g., 1-ethyl-3-(3-dimethyl amino propyl) carbodiimidehydrochloride, is added, in a freshly made solution with a minimum amount of water. This carbodiimide is added in an amount to provide a final concentration thereof in the order of about 0.1M. A pH below 7 is maintained for at least one hour, and the mixture is then stirred overnight or longer. The particles are washed alternatively in an aqueous buffer of low pH (about 4.0) then in an aqueous buffer of higher pH (about 8), and finally washed twice with distilled water. The beads containing coupled glycoprotein of this invention are then stored in the higher aqueous pH buffer (about 8) at concentrations of about 1%.

To conduct a test of infectious mononucleosis, glycoprotein-latex beads are diluted in buffer to a concentration in the order of about 0.25% (w/v). Appreciably lower concentrations of the reagent prevent agglutination that is easily visible, while appreciably higher concentrations result in waste of protein bound carrier particles. Serial dilutions in buffer are made of the test antiserum or biological fluid such as serum. One drop of each such dilution is added to one drop of the purified glycoprotein-latex bead reagent within the ceramic ring of a well in a serological ring slide. The slide is rotated briefly to mix antiserum or serum and latex reagent, and agglutination is determined by visual inspection. The end points of the titration are determined as the highest dilution (i.e., most dilute concentration) of serum giving visible clumping. Other containers may be used for the agglutination test, such as the polystyrene microfilm plates with U-shaped wells from Cooke Engineering Co., but agglutination is more difficult to read in such wells.

2. Immunoassay Using Purified Glycoprotein of This Invention.

Many types of immunoassays, including radioimmunoassays, are known in the art and can be employed for the detection and/or quantitation of purified glycoprotein of this invention. An immunoassay may use, for example, a radioactive tag for the antigen, such as $^{125}I$, $^{131}I$, $^{3}H$ or $^{14}C$, or any other radio isotope easily and conveniently measured. Other methods of tagging the antigen include attachment of a fluorogen, chromophore, enzyme or luminescent tag. Numerous methods of separating antibody-antigen complexes from free, (i.e. unbound) antigen are known, including precipitation of antibody (double antibody). Among other known techniques are those using solid support matrices, also known as a solid-phase assay wherein glass, silica or plastic beads or unitary plastic inserts are used to fix one component of the antigen-antibody pair.

A preferred way to tag purified glycoprotein of this invention is with $^{125}I$, a radioactive label that can yield labelled antigens with very high specific activity, as measured in terms of the rate of detectable disintegrations per microgram of protein.

The purified glycoprotein is labeled with $^{125}I$ to a specific activity of about 1 micro Curie/microgram of protein by one of a variety of methods known in the art such as e.g., lactoperoxidase, chloramine-T labeling, or Iodogen [Fraker, P. J. & J. C. Speck, *Biochem. Biophys. Res. Commun.* 80. 849 (1978)]. The labeled protein is separated from unreacted free $^{125}I$ by gel filtration with e.g., Sephadex G-50, Sephadex G-25, Sephadex G-10, or any of the porous polyacrylamide beads exhibiting molecular weight exclusion limits less than about 100,000.

A preferred immunoassay based on $^{125}I$-labeled purified glycoprotein, is the competitive radioimmunoassay. The principle of the competition radioimmunoassay is that labeled antigens compete with unlabeled antigens for the same combining sites of the antibody in the serum. See, e.g., Kabat, E. (1976) *Structural Concepts in Immunology and Immunochemistry* Holt, Richard and Winston. Separation of antibody-antigen complexes from free antigen allows the determination of the amount of antigen bound. This well-known assay has many variations, for example, testing a variety of unlabeled antigens to determine which unlabeled antigen has the greatest similarity to the labeled antigen. Another variation, used for the glycoprotein of this invention, is to test a standardized quantity of radio-labeled and unlabeled antigen against samples from each of many dilutions of a variety of test antisera with the purpose of obtaining a quantitative measure of the titer of specific antibody in any antiserum. This is done by determining the relative amount of radioactive antigen bound by the test antiserum and comparing this quantity with the amount bound by a control antiserum of the same dilution as the test antiserum.

It should be noted that variations within the scope of this invention also include competitive radioimmunoassays with $^{131}I$-, $^{3}H$-, or $^{14}C$-labeled glycoprotein, or competitive immunoassays using non-radioactive tags for glycoprotein such as a fluorogen, chromophore, luminescent material or enzyme.

There are many methods known in the art for separating antibody-antigen complexes from free antigen. One method usable with e.g. purified glycoproteins of this invention is the solid-phase, sandwich-type immunoassay. In this method, microtiter plates, preferably made of a material easily cuttable by scissors and with round bottom wells, are coated by incubation in each well of about two micrograms purified glyco-protein with about 200 microliters of aqueous buffered saline solution overnight. Most suitably this step is effected in a moist chamber to prevent drying.

The wells are then emptied by aspiration, washed at least once with aqueous buffered saline and filled with a solution of protein carrier in aqueous buffered saline. The protein carrier blocks any binding sites on the inside of the well, or the solid-phase, that were not bound by purified glycoprotein added in the first step. Typical solutions of protein carrier used for coating wells are e.g., gelatin, goat serum albumin, rabbit serum albumin, or egg ovalbumin in the concentration ranges of from about 0.05% to about 0.2%. The plates are incubated with carrier solution for at least one hour with gentle agitation or mixing to enhance uniform coating of the well.

The wells are then emptied again by aspiration, washed two to five times with aqueous buffered saline, preferably three times, and then about 200 microliters of suitably diluted serum sample is added to each well. This step binds the antigen to specific antibody. The plates are incubated to equilibrate the antibody with the antigen, for instance at room temperature overnight, preferably in a moist chamber to prevent drying.

The wells are emptied a third time by aspiration, washed about five times, then about 10,000 cpm (counts per minute) of $^{125}I$-purified glycoprotein suitably diluted in carrier protein (e.g., 0.1% egg ovalbumin in aqueous buffered saline) is added to each well in a total volume of about 200 microliters. Radiolabeled protein is allowed to equilibrate with binding sites on the antibody still available to the antigen, with, for example, an incubation overnight.

The contents of each well are aspirated for the fourth time, and each well washed at least three times with aqueous buffered saline. The plates are air dried about 6 hours, then their wells are cut out with scissors, and radioactivity is counted in a conventional counter. For $^{125}I$, one minute counts are normally sufficient for reasonable accuracy.

3. Lymphocyte Assays

The purified glycoprotein products of this invention were powerful inhibitors of E-rosette formation. Fifty percent inhibition of rosetting by human peripheral blood lymphocytes with sheep erythorcytes could be shown by the incubation of the lymphocytes with 80 micrograms of purified sheep erythrocyte glycoprotein or with only 30 micrograms of the purified horse erythrocyte glycoprotein. Bovine and human erythrocyte glycoprotein did not exhibit similar inhibition in experiments conducted by the applicant. Fifty percent inhibition was not achieved with either bovine or human erythrocyte glycoprotein at concentrations as high as 500 micrograms.

The inhibition of E-rosettes formation was accomplished by using standard techniques well known in the art.

The purified glycoproteins of this invention are also substantially useful reagents for enumerating and characterizing peripheral blood lymphocytes in other ways. For example, the glycoproteins may be tagged with $^{125}I$ or fluorogen and used to assay ligand receptor interaction. Alternatively, the glycoproteins may be coupled to inert particles for similar purposes. Thus, the glycoproteins of this invention may be used effectively as a substitute for red blood cells in standard assays for enumerating subpopulations of peripheral lymphocytes. The glycoprotein is also cheaper and more stable than antibody, a widely used reagent in tagged form for assaying lymphocytes.

While the invention has been described in connection with specific embodiments thereof, it will be understood that it is capable of further modification and that this application is intended to cover any variations, uses, or adaptations of the invention following, in general, the principles of the invention and including such departures from the present disclosure as come within the ordinary skill of the pertinent art within the art to which the invention pertains, and as may be applied to the essential features hereinbefore set forth, within the spirit of the invention and the scope of the appended claims.

The following examples further illustrate the products of this invention.

EXAMPLE 1

Preparation of Hemaglobin-free Stroma from Blood

Fresh blood was collected from sheep at the time of slaughter and from horse by veni puncture in an anticoagulent citrate-dextrose solution. The blood was held at 4° C. for about 24 hours and was centrifuged at about 2500 RPM for about twenty minutes at 4° C. to pellet erythrocytes. The supernatant and intermediate cell layer were removed. The erythrocytes were washed three times in an equal volume of cold 0.12M NaCl, 0.05 sodium phosphate buffer, about pH 7.4.

For each washing step, the cells were resuspended in buffer, then centrifuged at about 2500 RPM for about twenty minutes. After centrifugation, the supernatant and remaining buffy coat were aspirated. This procedure was repeated three times resulting in a 25% loss in the total volume of erythrocytes in order to remove the buffy coat.

EXAMPLE 2

Isolation and Purification of Erythrocyte Glycoprotein

Washed erythrocytes were lysed into nine volumes of cold 0.005 M sodium phosphate at a pH of about 8.0. The membranes were pelleted by centrifugation at 13,000 x g for 45 minutes at 4° C. The supernatant was aspirated and discarded. The cell membrane layer was then decanted from the red pellet. The procedure described above was repeated until the membranes were a creamy white color. The membranes were sequentially extracted under reflux with acetone, absolute alcohol and with 75% ethanol. The 75% ethanol extract was concentrated to a small volume by vacuum distillation, dialyzed and freeze-dried. This was the crude extract which was further purified in a series of steps. The 75% ethanol extract was precipitated from ethanol, then dissolved in 0.02 M sodium citrate, pH 4.1 and placed on a phosphocellulose column equilibrated and eluted with the same buffer. The column effluent was monitored for sialic acid, hexose and optical density at 280 nanometers. The sialic acid fraction emerged in the void volume and was dialyzed. Glycoprotein, at a concentration in water of 2 mg/ml was mixed for thirty minutes at 0° C. with 5 volumes of diethyl ether:ehtanol (4:1 volume/volume). The aqueous phase was lyophilized and extracted again with diethyl ether:ethanol. Glycoprotein, at a concentration of 10 mg/ml water was extracted with nine volumes of chloroform:methanol (2:1 volume/volume) for 30 minutes at 23° C. and was centrifuged at 2000 RPM for 30 minutes. The aqueous layer was lyophilized and dissolved in 0.05M Tris-HCL buffer at pH of 8.0 containing 1% Emulphogene BC-720 (GAF, New York, N.Y.) and placed on a Whatman DE-52 cellulose column equilibrated with 0.5 M Tris-HCL buffer at pH 8.0. This column was eluted with a 0.0→0.5 M NaCl gradient buffer. The purified glycoprotein eluted as a single peak and was dialyzed and freeze-dried.

EXAMPLE 3

Erythrocyte Glycoprotein-latex Bead Reagent Bead

The purified erythrocyte glycoprotein isolated as in example 2 above, was coupled to a 0.25% suspension in water of carboxyl-modified uniform latex particles, 0.455 micron average diameter (Dow Diagnostics). The mixture was stirred with the pH maintained as 5±1 for 30 minutes at 22° to 25° C. Then 1-ethyl-3-(3-dimethylaminopropyl) carbodimide-hydrochloride, freshly dissolved in a minimum amount of water, was added to a final concentration of 0.1 M. The pH was maintained at 5.5 for 1 hour, and the mixture was stirred at 22° to 25° C. for 18 hours. The particles were then washed alternatively in a buffer containing 0.1 M glycine, 0.15 M NaCl, 7mM $CaCl_2$ (GBS) at pH 4.0 and then at pH 8.0 and twice with distilled water. Between each wash the particles were centrifuged at 17,000X g for 20 minutes. The glycoprotein latex bead reagent was then diluted to a concentration of 1% in GBS at pH 8.3 and stored at 4° C. Before use, the reagent was diluted to 0.25% with GBS.

EXAMPLE 4

Latex slide test with glycoprotein latex coupled beads

The glycoprotein-latex bead reagent of Example 3 was used in a latex test carried out on serological ring slides, 7.9 by 12.1 cm (Scientific Products). Serial doubling dilutions of test sera were done in GBS (pH 8.3). One drop of each dilution of serum was then added to one drop of the glycoprotein latex bead reagent within a ceramic ring on the slide. The slide was rotated on a Thomas Clinical Rotater at 1,500 RPM for 5 minutes at 22° to 25° C., and agglutination was determined by microscopic examination. The endpoints of titration were recognized as the highest dilution of serum giving visible clumping as compared to a control latex suspension.

EXAMPLE 5

Purified glycoprotein labelled with $^{125}I$

One hundred micrograms of the purified glycoprotein from Example 2 is labelled with 100 microcuries of $^{125}I$ A 20 microliter aliquot of methylene chloride solution containing 0.4 micrograms 1,3,4,6—tetrachloro—$3a,6a$—diphenyl glycoluril (11 a) (Pierce Chemical Co., Rockford, Ill.) is placed in a test tube, and the methylene chloride is evaporated by rotating the tube in a 37° C. bath so that a thin film of II a forms in the bottom. To another test tube is added, in pH 8.2 borate-saline buffer, 100 micrograms of the purified glycoprotein, 0.11 micrograms of potassium iodide and 100 microcuries of $^{125}I$; the final volume of this mixture is adjusted to 100 μl with borate-saline buffer. After bringing the tubes to 0°-2° C., reaction is initiated by transferring the glycoprotein solution to the tube containing II a. The reaction is allowed to proceed for 5 minutes at 0°-2° with gentle stirring; it is terminated by decanting the mixture from the residual glycouril. For determining the efficiency of iodination, 5 microliter aliquots of the reaction mixture are mixed with 0.1 mg of bovine serum albumin, in 10 microliters of borate-saline, and then with 1 milliliter of cold 10% trichloroacetic acid. After standing for 30 minutes at 0°-2°, these mixtures are centrifuged. The pellets are mixed with 1 milliliter of fresh 10% trichloroacetic acid, and the mixtures are centrifuged again. The protein precipitates are then dissolved in 1 milliliter of 0.1 M sodium hydroxide. The labelled protein is separated from free iodine by chromatography on Sephadex G-50 column. The specific activity is 1 microCurie per microgram glycoprotein.

EXAMPLE 6

Glycoprotein Radioimmunoassay

This solid-phase, sandwich type immunoassay uses the purified glycoprotein of Example 2. The wells of polystyrene microtitre plates (U-bottom, Cooke Engineering Co., U.S.A.) were coated with purified glycoprotein by incubating with 2 micrograms of the purified glycoprotein in 200 microliters of phosphate-buffered saline (PBS). The plates incubated overnight at 22°-25° C. in a moist chamber. The wells were emptied by aspiration and washed three times in PBS. Then the wells were filled with 0.1% gelatin in PBS and incubated at 22°-25° C. for 1 hour on a Cortis Laboratories micromixer. The wells were then emptied by aspiration, washed three times in PBS and 200 microliters of suitably diluted serum was added to each well. The plates were incubated overnight at 22°-25° C. in a moist chamber The wells were emptied and washed in two liters of PBS with mixing. The $^{125}I$-labelled erythrocyte glycoprotein suitably diluted in 0.05% bovine serum albumin (BSA) in PBS was added to each well in a volume of 200 microliters. The plates were incubated overnight. The contents of each well were aspirated and washed three times with PBS. The plates were air dried. Each well was cut out with scissors and radioactivity counted in a gamma scintillation counter.

EXAMPLE 7

E-Rosette Inhibition Assay

Human lymphocytes were isolated from samples of peripheral heparinized venous blood. The lymphocytes were isolated by gradient centrifugation. The lymphocyte isolation was carried out by layering the blood, which had been diluted 1:2 with RPMI medium, above lymphocyte separation medium (LSM, Litton Bionetics). The tubes were centrifuged at about 400 x g for about 45 minutes. Mononuclear cells were collected from the interphase, washed and counted. Various amounts of glycoprotein were incubated with the peripheral blood lymphocytes at about 20° C. for about 30 minutes. Washed sheep erythorocytes were then added to effect a ratio of erythrocytes to peripheral blood lymphocytes of 40:1. The mixture was centrifuged at about 200x g for about 5 minutes at about 20° C. then incubated at about 40° C. overnight before rosettes were counted. Three or more erythrocytes attached to a lymphocyte were considered a rosette.

What is claimed is:

1. A mammalian erythrocyte glycoprotein selected from the group consisting of horse and sheep erythrocyte glycoprotein, the amino acid composition of the horse erythrocyte glycoprotein being about 8.1 mole % aspartic acid, about 10.6 mole % threonine, about 10.8 mole % serine, about 9.4 mole % glutamic acid, about 12.3 mole % proline, about 9.2 mole % glycine, about 11.3 mole % alanine, about 4.4 mole % valine, about 0.8 mole % methionine, about 3.5 mole % isoleucine, about 8.2 mole % leucine, about 1.1 mole % tyrosine, about 2.9 mole % phenylalanine, about 1.2 mole % histidine, about 1.3 mole % lysine and about 4.8 mole % arginine, and the amino acid composition of the sheep erythrocyte glycoprotein being about 5.6 mole % aspartic acid, about 8.1 mole % threonine, about 12.9 mole % serine, about 13.0 mole % glutamic acid, about 11.6 mole % proline, about 7.7 mole % glycine, about 9.6 mole % alanine, about 6.2 mole % valine, about 0.5 mole % methionine, about 4.6 mole % isoleucine, about 8.3 mole % leucine, about 4.6 mole % in tyrosine, about 1.2 % phenylalanine, about 1.6% histidine, about 3.2 mole % lysine, about 4.0 mole % arginine, and about 0.3% tryptophan.

2. A horse erythrocyte glycoprotein according to claim 1, the amino acid composition of which is about 8.1 mole % aspartic acid, about 10.6 mole % threonine, about 10.8 mole % serine, about 9.4 mole % glutamic acid, about 12.3 mole % proline, about 9.2 mole % glycine, about 11.3 mole % alanine, about 4.4 mole % valine, about 0.8 mole % methionine, about 3.5 mole % isoleucine, about 8.2 mole % leucine, about 1.1 mole % tyrosine, about 2.9 mole % phenylalanine, about 1.2 mole % histidine, about 1.3 mole % lysine and about 4.8 mole % arginine.

3. A sheep erythocyte glycoprotein according to claim 1, the amino acid composition of which is about 5.6 mole % aspartic acid, about 8.1 mole % threonine, about 12.9 mole % serine, about 13.0 mole % glutamic acid, about 11.6 mole % proline, about 7.7 mole % glycine, about 9.6 mole % alanine, about 6.2 mole % valine, about 0.5 mole % methionine, about 4.6 mole % isoleucine, about 8.3 mole % leucine, about 4.6 mole % tyrosine, about 1.2 mole % phenylalanine, about 1.6 mole % histidine, about 3.3 mole % lysine, about 4.0 mole % arginine, and about 0.3 mole % tryptophan.

4. A horse erythrocyte glycoprotein according to claim 2 which is a sialoglycoprotein comprised of about 55% carbohydrate residues in a composition of about 28 grams of N-glycolylneuraminic acid, about 11 grams of galactose, about 14 grams of N-acetylgalactosamine, about 1 gram of N-acetylglucosamine and about 1 gram of mannose per 100 grams of glycoprotein.

5. The horse erythrocyte glycoprotein of either of claims 2 and 4 which is essentially homogenous.

6. A horse erythrocyte glycoprotein according to either of claims 2 and 4, containing a label selected from the group consisting of radioisotopes, fluorogens, chromophores, enzymes, luminescent substances and other known labels used in immunoassay procedures.

7. The labelled horse glycoprotein of claim 6 which is labelled with $^{125}I$.

8. A sheep erythrocyte glycoprotein according to claim 3 which is a sialoglycoprotein comprised of about 56% carbohydrate residues in a composition of about 17 grams of sialic acids, about 9 grams of galactose, about 14 grams of N-acetylgalactosamine, about 14 grams of N-acetylglucosamine, and about 2 grams of mannose per 100 grams of glycoprotein.

9. The sheep erythrocyte glycoprotein of any of claims 1, 3 and 8 which is essentially homogeneous.

10. A sheep erythrocyte glycoprotein according to any of claims 1, 3 and 8 containing a label selected from the group consisting of radioisotopes, fluorogens, chromophores, enzymes, luminescent substances and other known labels used in immunoassay procedures.

11. The labelled sheet glycoprotein of claim 10 which is labelled with $^{125}I$.

12. A process for preparing the mammalian glycoproteins of claim 1 which comprises the steps of:
 (a) uniformly suspending dried, ground, hemoglobin-free stroma from mammalian erythrocytes in anhydrous acetone;
 (b) refluxing for from about 1 to about 6 hours, filtering and drying the residue;
 (c) suspending said dried residue in 100% anhydrous ethanol;
 (d) refluxing between about 1 and about 6 hours, filtering and drying the residue;
 (e) suspending the dried residue from step (d) in aqueous ethanol of between about 50% and about 80% strength, and repeating step (b);
 (f) dissolving the residue from step (e) in water and adding 90% aqueous ethanol, followed by incubating on ice until crystallization occurs, centrifuging and dialyzing the solid layer against a low pH, low ionic strength buffer;
 (g) passing the solid from step (f) through a cation exchange resin on a chromatographic column;
 (h) collecting the sialic acid containing fractions from the column and drying them;
 (i) treating the collected fractions from step (h) by extraction with a known lipid solvent, centrifuging, collecting the aqueous layer and drying it;
 (j) repeating step (i) on the product of that step, using a different lipid solvent;
 (k) recovering the product of step (j) in lyophilized form;
 (l) dissolving the product of step (k) in a low ionic strength buffer containing about 1% neutral detergent;
 (m) loading the solution from step (l) on an anion exchange chromatographic column;
 (n) washing the column thoroughly with low ionic strength buffer;
 (o) eluting the column with aqueous buffer to high salt concentration; and
 (p) dialyzing the product of step (o) against water and recovering the product in freeze dried form.

13. A process according to claim 12 wherein the cation exchange resin is phosphocellulose.

14. A process according to claim 12 wherein the lipid solvent of step (i) is diethyl ether and ethanol in a volume ratio between about 4:1 and about 1:1.

15. A process according to claim 12 in which the lipid solvent of step (j) is chloroform and methanol in a volume ratio of about 2:1.

16. A process according to claim 12 wherein the solvent in step (e) is about 75% aqueous ethanol.

17. A process for the inhibition of rosetting by human blood lymphocytes which comprises incubating said lymphocytes with the horse erythrocyte glycoprotein of either of claims 2 or 4.

18. A process for the inhibition of rosetting by human blood lymphocytes which comprises incubating said lymphocytes with the sheep erythrocyte glycoprotein of either of claims 3 or 8.

19. A process for monitoring or diagnosing human infectious mononucleosis the improvement which comprises utilizing the horse erythrocyte glycoprotein of either of claims 2 or 4 as an inhibitor of agglutination.

20. A process for monitoring or diagnosing human infectious mononucleosis the improvement which comprises utilizing the sheep erythrocyte glycoprotein of either of claims 3 or 8 as an inhibitor of agglutination.

* * * * *

UNITED STATES PATENT AND TRADEMARK OFFICE
CERTIFICATE OF CORRECTION

PATENT NO. : 4,525,459
DATED : June 25, 1985
INVENTOR(S) : Mary A. Fletcher

It is certified that error appears in the above-identified patent and that said Letters Patent is hereby corrected as shown below:

Column 15, line 3, period is missing after "$^{125}I$".
Column 16, line 47, Claim 3, "erythocyte" should read
--erythrocyte--.

Signed and Sealed this

Sixth Day of May 1986

[SEAL]

Attest:

DONALD J. QUIGG

Attesting Officer    Commissioner of Patents and Trademarks